United States Patent [19]

Lambert

[11] Patent Number: 5,250,066
[45] Date of Patent: Oct. 5, 1993

[54] PLASTIC POINTED ARTICLES AND METHOD FOR THEIR PREPARATION

[75] Inventor: James M. Lambert, Centerville, Ohio

[73] Assignee: Becton Dickinson and Company, Franklin Lakes, N.J.

[21] Appl. No.: 495,670

[22] Filed: Mar. 19, 1990

[51] Int. Cl.$^5$ .................................... A61B 17/32
[52] U.S. Cl. .................... 606/181; 606/167; 604/272
[58] Field of Search ............. 604/239, 272; 606/181, 606/182, 183, 167, 222, 223

[56] References Cited

U.S. PATENT DOCUMENTS

| | | | |
|---|---|---|---|
| 2,512,568 | 6/1950 | Saffir | 604/239 |
| 4,545,376 | 10/1985 | Beiter | 606/181 |
| 4,677,979 | 7/1987 | Burns . | |
| 4,712,548 | 12/1987 | Enstrom | 606/181 |
| 4,795,446 | 1/1989 | Fecht | 604/264 |
| 4,936,827 | 6/1990 | Grimm et al. | 604/60 |

FOREIGN PATENT DOCUMENTS

| | | | |
|---|---|---|---|
| 0017999 | 10/1980 | European Pat. Off. | 606/181 |
| 0137975 | 4/1985 | European Pat. Off. . | |
| 0271775 | 6/1988 | European Pat. Off. | 604/239 |
| 2164363 | 7/1973 | Fed. Rep. of Germany | 604/239 |
| 3323867 | 1/1985 | Fed. Rep. of Germany | 604/272 |
| 1039161 | 10/1953 | France | 604/272 |
| 2641963 | 7/1990 | France | 606/181 |

Primary Examiner—C. Fred Rosenbaum
Assistant Examiner—Mark O. Polutta
Attorney, Agent, or Firm—Richard E. Brown

[57] ABSTRACT

A plastic article having a sharp point is made of a polymer of high impact strength and high hardness. The article may be a lancet or a needle for skin puncture, suturing or sewing. A method for preparing the article includes shear thinning a melt of a polymer and introducing the shear thinned melt into a mold which includes a sharp point.

5 Claims, 1 Drawing Sheet

PLASTIC POINTED ARTICLES AND METHOD FOR THEIR PREPARATION

BACKGROUND OF THE INVENTION

1. Field of the Invention

This invention relates to a plastic article having a sharp point, and more particularly relates to a medical article for tissue penetration and a method for its preparation.

2. Background

Many articles require a sharp point for penetration of a substrate or a material. Such articles may, for example, be in the form of a solid needle used in sewing or, in the surgical arena, for suturing. In the medical arts, articles having a sharp point, known as lancets, are used to finger prick a patient's skin to draw a small blood sample.

Lancets have been employed for many years to make a quick puncture or penetration of a patient's skin in order to provide a small outflow of blood. Various tests may be employed with only a small amount of blood so that the blood flowing from a finger prick is normally sufficient to carry out a substantial number of tests. However, due to the sensitive nerve endings in the fingertip area, this procedure sometimes induces a significant amount of pain in the patient, even though the skin puncture produces minimal cutting. Moreover, as will be understood, many people are frightened by the appearance of a blade or skin puncturing apparatus of any kind wherein the cutting portion is visible to them prior to the puncture. In order to minimize potential pain, as well as to reduce apprehension in a patient, it is desirable to make the thrust of the lancet through the patient's skin as accurately and rapidly and withdrawal from the skin as quickly and quietly as possible. As a result, a variety of designs for lancets which have structure for automatic thrust and withdrawal have been disclosed, as exemplified by Burns in U.S. Pat. No. 4,677,979.

Hitherto, needles and lancets have primarily been made of metal, most often stainless steel, to impart the desired stiffness and strength. Metal needles, however, are manufactured by a multi-step process which includes drawing a metal rod to the proper size, cutting, sharpening, etching, cleaning, assembling, and connecting to a plastic holder portion. In construction of articles of the type utilized by the medical profession, it is often necessary to connect dissimilar materials. This creates problems in those instances where the dissimilar materials are not readily receptive for interconnection. For example, some plastics such as polytetrafluoroethylene do not bond well to metal components because of the resistance of polytetrafluoroethylene to most epoxies.

It is evident that medical grade articles intended for tissue penetration will of necessity be expensive. For example, a lancet consisting of a stainless steel blade attached to a plastic holder costs about five cents, a prohibitive cost for a single-use, throwaway item used in quantity as is favored in today's medical practice.

Because of the above drawbacks of metal needles and lancets, much effort has been expended in attempts to fabricate these items by single step injection molding of low cost plastics. Applicants are aware of a plastic lancet of injection molded polyacetal. This material, however, is soft and compliant and undesirable for plastic puncture tips because its flexibility requires a substantially perpendicular angle between the point and the finger to prevent bending and unsuccessful puncture. Accordingly, the aforementioned polyacetal lancet is molded in the shape of a tetrahedron to overcome the flexibility. This, however, causes cutting by four edges rather than the two cutting edges of conventional beveled points and leads to increased pain for the patient.

Accordingly, there is a very real need in the medical profession for a lancet capable of penetrating a patient's skin with minimum discomfort yet which is sufficiently inexpensive for economical single use. The present invention is directed to fulfillment of this need.

SUMMARY OF THE INVENTION

One aspect of the invention is a plastic article terminating in a sharp point molded from a polymer of high impact strength and hardness. The article may be a lancet for puncturing the skin of a patient, a needle used in sewing or suturing or an insertion device for a catheter. Preferred articles are integral and include a body portion for grasping and a needle portion terminating in the sharp point.

The polymer of the article is thermoplastic and forms a melt of sufficiently low viscosity to completely fill a mold which narrows down to a sharp point. Preferred polymers are liquid crystalline polymers and impact resistant acrylics.

Another aspect of the invention is a method for preparing the article of the invention. The method includes forming a melt of the polymer of sufficiently low viscosity to completely fill a mold which includes a sharp point, cooling the melt and removing the article from the mold. A preferred method includes shear thinning the polymer melt, preferably under pressure, to achieve the desired viscosity prior to filling the mold. In the present disclosure, the term shear thinning describes the well-known propensity of most polymer melts to undergo a reduction in viscosity when subjected to conditions of high shear.

Thus, the invention provides an article of a thermoplastic polymer, such as a lancet or a needle, having a point sharp enough to penetrate a patient's skin without causing substantially more discomfort to the patient than use of a conventional stainless steel needle. The article of the invention is manufactured by injection molding so that it can be of any desired shape depending on the mold selected. Injection molding is a simple, efficient and inexpensive process readily adapted to mass production which greatly reduces the cost of the article relative to similar articles prepared from other materials by other processes.

The high impact strength, high hardness polymers useful in the invention have exceptional tensile strength, low brittleness and high bend modulus properties very desirable in a needle. Further, the liquid crystal article has a very low-friction surface which facilitates mold release and greatly contributes to patient comfort when used for skin penetration.

DETAILED DESCRIPTION

Figure 1:
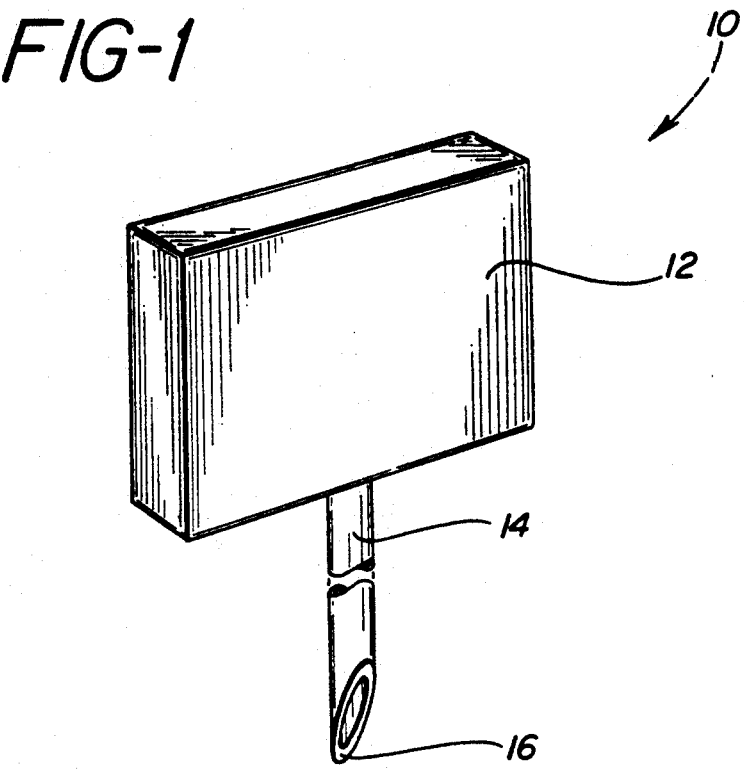
FIG. 1 is a perspective view of a lancet of the invention.
Figure 2:
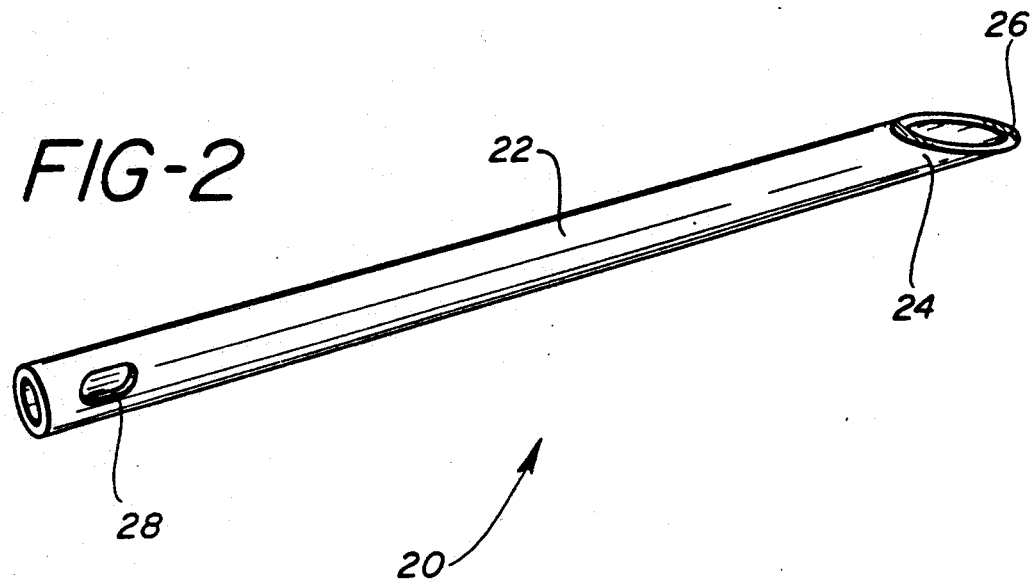
FIG. 2 is a perspective view of a needle of the invention.

While this invention is satisfied by embodiments in many different forms, there will herein be described in detail preferred embodiments of the invention, with the understanding that the present disclosure is to be considered as exemplary of the principles of the invention and is not intended to limit the invention of the embodiments illustrated and described. The scope of the invention will be measured by the appended claims and their equivalents.

In accordance with the present invention, plastic devices tapering to a sharp point are fabricated from hard, thermoplastic polymers of high impact strength by injection molding techniques. It has been found that melts of such polymers, preferably after shear thinning, will completely fill a mold, including the tip, whereby a unitary plastic device having a sharp tip may be made in a single molding operation.

Without wishing to be limited thereby, representative devices of the invention are finger-prick lancets, solid needles, introducers for catheters and hypodermic needles. A preferred device is a lancet comprising a body portion for grasping and a needle portion having a tip sharp enough to penetrate a patient's skin without substantial discomfort or attendant breaking or bending.

Adverting now to the drawings for a more detailed description of the device of the invention, the figures show a lancet 10 and a needle assembly 20. Lancet 10 has integral body portion 12 for grasping and needle portion 14 projecting therefrom and tapering to beveled point 16. Needle assembly 20 has body portion 22 and needle portion 24 tapering to point 26 and may optionally include an eye 28.

It is not intended that the device of the invention be limited to the shapes illustrated in the drawings. Thus, body portion 12 of lancet 10, while shown to be rectangular, may be of any shape convenient for grasping by a technician or insertion into an automatic lancet device. Likewise, the body portion 22 of needle 20, while shown to be cylindrical, may be of any other convenient shape. The needle point, while illustrated to have the preferred beveled shape, may be of any suitable design. It is also evident that the article may have other integrally molded parts which may be useful for the particular use intended for the article.

Polymers which may be used for molding the article of the invention have high impact strength and durometer hardness. Impact strength is an art term substantially synonymous with nonbrittleness meaning the ability of the material to accept a sudden blow or shock without fracture. Impact strength may be determined by Izod testing using ASTM procedure D256. Durometer hardness may be determined by ASTM procedure D2240. In accordance with the invention, it has been found that thermoplastic polymers or mixtures thereof having a durometer hardness of at least 70 Shore D and an Izod impact strength of at least 1.0 ft-lb/in are suitable for the article of the invention.

Without being limited thereby, the following list of commercially available polymers may be used: 1) liquid crystalline polymers, preferably polyesters, such as Vectra TM (Hoechst-Celanese, Chatham, N.J.), Xydar TM (Amoco Performance Products, Ridgefield, Conn.), and LCP TM (RTP Co., Winona, Minn.); 2) modified acrylic, such as Plexiglas TM MI-7 (Rohm and Haas Co., Philadelphia, Pa.); 3) impact resistant polystyrene such as Rovel TM, (Dow Chemical Co., Midland, Minn.), and H5M polymer (Amoco Chemical Co., Chicago, Ill.); 4) impact resistant polycarbonate such as Xenoy TM, (General Electric Co., Pittsfield, Mass.); and 5) polyurethane having a hard segment content of 90% or greater such as Isoplast TM, (Dow Chemical, Midland, Mich.).

It has been found, as described later, that liquid crystalline polymeric articles of the invention have certain processing advantages over other polymers. However, in terms of overall performance and unit cost, the most preferred material at the present time is modified acrylic.

The molecules in melts of most polymers exist in a completely random state. It is known that when polymeric melts are passed through an orifice, the elongated molecules of the polymer orient themselves into an arrangement in which they are aligned substantially completely in the direction of melt flow and thereby undergo a reduction in viscosity, a process conventionally known as shear-thinning. In accordance with the invention, it has been found that shear thinned polymeric melts will flow into and completely fill a mold which includes a sharp tip.

When the polymers of high impact strength and hardness as defined above are melted, shear-thinned, directed into a pointed mold and cooled, the polymer retains its mechanical properties. Thus, in accordance with the invention, the article of the invention, by combining hardness and impact strength, exhibits low flex or bend modulus and low elongation so that the point will puncture the skin rather than bend, and high tensile strength and impact strength to prevent the point from breaking off during or after penetration.

The tensile strength of the molded polymer may be about 8,000 to 70,000 psi, preferably about 25,000 to 35,000 psi. Elongation to break may be about 1 to 50, preferably about 2 to 20%. The flex modulus may be about 500,000 to 20,000,000, preferably about 800,000 to 7,000,000 psi. For comparison purposes, these properties for stainless steel are about 100,000 psi, 50% and 28,000,000 psi respectively. For ordinary polystyrene, a product totally unsuitable for the article of the invention because of its brittleness, the values are about 6,000 psi, 2% and 480,000 psi respectively.

For ease in removal of the molded article from the mold, a conventional mold releasing agent, such as Sprayon (Sherwin-Williams) or Fluorocarbon Release Agent Dry Lubrican (Miller-Stephenson) may preferably be used. Articles molded from shear thinned liquid crystalline polymers have a very low coefficient of friction, generally in the range of 0.1 to 0.25. This property enables the liquid crystalline article of the invention to release from the mold without any mold releasing agents.

Another aspect of the invention is a method to prepare plastic articles having a sharp point. In its broadest scope, the method includes melting a thermoplastic polymer and introducing the melt into an injection mold of the desired shape in a conventional molding operation. Molding may be performed at any temperature between the melting and decomposition temperatures of the polymer at which the viscosity of the melt is sufficiently low to enable the melt to completely fill the mold. To attain the highest molecular orientation and mechanical properties, a liquid crystalline polymer should be processed within its anisotropic melt range.

In a preferred method of the invention, the polymer melt may be forced under pressure through an orifice and thence directly into the mold. Passage of the melt through the orifice effects shear thinning and reduces the viscosity of the melt to facilitate complete filling of the mold.

Alternatively, the melt may be shear thinned, as known in the art, by blending the melt with a shear thinning additive such as poly($\alpha$-methylstyrene) (PAMS). The PAMS may be blended into the melt in about 1 to 10, preferably about 2 to 4, weight percent.

The degree of shear thinning is a function of the nature of the polymer, the temperature, the pressure applied, if any, and thus the rate of passage through the orifice, and the size of the orifice. These variables are well-known in the injection molding art, and a suitable combination of thinning and molding conditions may easily be determined by those skilled in the art. Thus, without wishing to be limited thereby, preferred molding parameter ranges are a pressure of 500 to 1,500 psi, a shear rate of 10 to 150 sec$^{-1}$, and an orifice size of 0.5 to 2.0 mm. After shear thinning, the polymer melt flows into and completely fills the mold, including the tip.

After release from the mold, the molded point of the article is generally sharp enough to puncture a patient's skin with minimum discomfort. If desired, however, the molded point may be machined by any conventional procedure such as grinding, sanding, or may be thermoformed in a heated tipping die to further sharpen the point. A conventional lubricant may be then applied to its surface. Liquid crystalline articles of the invention often have sufficient inherent lubricity to allow skin puncture without any lubricant.

The finished article may then be sterilized by any convenient procedure, such as chemical, heat or irradiation.

EXAMPLE I

General Procedure for Molding Plastic Pointed Articles

The polymer was melted and forced at a suitable temperature and pressure through a die having a circular orifice of about 1.6 mm diameter. The die was mounted on a conventional injection molding apparatus so that the polymer, after passing through the orifice, flowed directly into a needle mold having a beveled point. After filling, the mold was cooled and the article was removed. It was found that the needle had a point which was comparable in penetration force to a Microfine TM stainless steel lancet (Becton, Dickinson and Company) when tested in accordance with the procedure of Example III.

EXAMPLE II

Plastic lancets having sharp beveled points were prepared as described in Example I from various polymers. Penetration forces of these lancets are given in Table I.

TABLE I

| POLYMER | TIP PENETRATION FORCE[a] (grams) | PENETRATION FORCE[b] (grams) |
| --- | --- | --- |
| 1. Vectra TM | 19 | 20 |
| 2. Polyacetal | 7 | 15 |
| 3. Isoplast TM 301 | 7 | 17 |
| 4. Plexiglas TM MI-7 | 10 | 17 |

TABLE I-continued

| POLYMER | TIP PENETRATION FORCE[a] (grams) | PENETRATION FORCE[b] (grams) |
| --- | --- | --- |
| 5. Microfine TM [c] | — | 11 |

[a]The initial force the cutting edge (beveled point) exerts when cutting through the test material.
[b]The force required for 50% of the lancet to penetrate into the test material.
[c]Stainless steel control lancet (Becton, Dickinson and Company).

EXAMPLE III

Measurement of Penetration Force

The plastic lancet was gripped in the upper jaw of the Instron Universal Testing Machine Model 1122 and lowered into the surface of an arbitrary penetration medium (a disposable polyethylene 1 mm thick glove) at a crosshead speed of 10 mm/min. The force required for initial tip penetration was recorded. The lancet was then advanced into the penetration medium until one half of the tip had penetrated and the required force measured again.

EXAMPLE IV

Measurement of Catastrophic Failure

Non brittleness or break resistance of the plastic lancet article was tested in a yes-no format. Using the setup and instrumentation as described in Example III, the point of the plastic lancet was lowered into the surface of a flat steel plate at a crosshead speed of 20 mm/min. If the tip fragmented, shattered or otherwise broke apart, a "yes" to catastrophic failure was assigned. If the tip bent but stayed in one piece, a "no" to catastrophic failure was assigned. The results of this experiment are given in Table II.

TABLE II

| Polymer | Catastrophic Failure |
| --- | --- |
| 1) Vectra ® | No |
| 2) Plexiglas TM MI-7 | No |
| 3) Polystyrene* | Yes |
| 4) Microfine TM | No |

*PS 202 (Huntsman Chemical Co., Chesapeake, Virginia)

Thus, the invention provides plastic articles having a point sufficiently strong, nonbrittle and sharp for comfortable penetration of a patient's skin with no danger of bending or breaking during use. The articles are made by a simple and economical injection molding process.

What is claimed is:

1. A lancet comprising a body portion and a needle portion tapering to a point, said body and needle portions being unitary and molded of a shear-thinned thermoplastic polymer selected from the group consisting of a liquid crystalline polymer and modified acrylic polymer.

2. The lancet of claim 1 wherein said point is beveled.

3. The lancet of claim 1 further comprising a shear thinning additive.

4. A lancet comprising a grasping portion and a needle portion having a point, said grasping and needle portions being unitary and molded of a shear-thinned thermoplastic, modified acrylic polymer having a durometer hardness of at least 70 Shore D and an impact strength of at least 1.0 ft-lbs/in.

5. A lancet prepared by a process comprising heating a thermoplastic modified acrylic polymer having an impact resistance of at least 1.0 foot pound per inch and a Shore D hardness of at least 70 to give a melt, forcing said melt through an orifice of about 0.5 to 2.0 mm diameter at a pressure of 500 to 1,500 pounds per square inch to give a melt of reduced viscosity, directing said melt of reduced viscosity into a mold having a beveled point whereby said melt of reduced viscosity completely fills said mold, and cooling said melt.

* * * * *